United States Patent
Regensburger

(10) Patent No.: US 12,102,395 B2
(45) Date of Patent: Oct. 1, 2024

(54) SYSTEM FOR POSITIONING A MEDICAL OBJECT AT A DESIRED DEPTH AND METHOD FOR EMITTING A LIGHT DISTRIBUTION

(71) Applicant: Siemens Healthcare GmbH, Erlangen (DE)

(72) Inventor: Alois Regensburger, Poxdorf (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/204,939

(22) Filed: Jun. 1, 2023

(65) Prior Publication Data

US 2023/0389993 A1   Dec. 7, 2023

(30) Foreign Application Priority Data

Jun. 2, 2022   (DE) ..................... 10 2022 205 662.0

(51) Int. Cl.
 *A61B 34/20*  (2016.01)
 *A61B 34/10*  (2016.01)
 *A61B 90/00*  (2016.01)

(52) U.S. Cl.
 CPC ........ *A61B 34/20* (2016.02); *A61B 2034/107* (2016.02); *A61B 2034/2055* (2016.02);
 (Continued)

(58) Field of Classification Search
 CPC ............................................. A61B 2034/2055
 See application file for complete search history.

(56) References Cited

U.S. PATENT DOCUMENTS 11,600,012 B2 * 3/2023  Mayer ................... G06T 19/006
2009/0124891 A1   5/2009  Shechter
(Continued)

FOREIGN PATENT DOCUMENTS

CH          716059 A2 * 10/2020   ............. A61B 34/20
CN       106061443 A    10/2016
(Continued)

OTHER PUBLICATIONS

Decision to Grant for German Application No. 10 2022 205 662.0 mailed Jun. 3, 2022, with English translation.
(Continued)

*Primary Examiner* — Zade Coley
(74) *Attorney, Agent, or Firm* — Lempia Summerfield Katz LLC

(57) ABSTRACT

A system for positioning a medical object at a desired depth includes a light guiding facility and a processing unit. The processing unit is configured to receive planning information that specifies a desired depth for an arrangement of a predefined section of a medical object in an examination object with respect to an entry point of the medical object in the examination object. The medical object has a mark that has a predefined relative positioning with respect to the predefined section. The processing unit is configured to control the light guiding facility for emitting a light distribution as a function of the planning information and the predefined relative positioning such that the light distribution illuminates the mark if the predefined section is arranged at the desired depth.

10 Claims, 7 Drawing Sheets

(52) U.S. Cl.
CPC . *A61B 2090/062* (2016.02); *A61B 2090/3764* (2016.02); *A61B 2090/3937* (2016.02)

(56) References Cited

U.S. PATENT DOCUMENTS

| | | |
|---|---|---|
| 2013/0218024 A1 | 8/2013 | Boctor |
| 2014/0218366 A1* | 8/2014 | Kosmecki ............... G06T 11/60 |
| | | 345/426 |
| 2015/0018842 A1* | 1/2015 | Rahimian ............... A61B 5/066 |
| | | 901/47 |
| 2015/0182725 A1 | 7/2015 | Finger |
| 2019/0096084 A1* | 3/2019 | Mayer ....................... G06T 7/70 |
| 2019/0314093 A1* | 10/2019 | Crawford ............... A61B 90/98 |
| 2021/0228308 A1 | 7/2021 | Berger et al. |
| 2023/0131750 A1* | 4/2023 | Joshi ....................... G06T 11/00 |
| | | 600/424 |

FOREIGN PATENT DOCUMENTS

| | | | |
|---|---|---|---|
| CN | 205625926 U | 10/2016 | |
| CN | 113180593 A | 7/2021 | |
| DE | 102019211870 A1 | 9/2020 | |
| RU | 2008143211 A | 5/2010 | |
| WO | 2013055707 A1 | 4/2013 | |
| WO | WO-2014113401 A1 * | 7/2014 | ............. B65G 43/08 |

OTHER PUBLICATIONS

Decision to Grant for German Application No. 10 2022 205 662.0 mailed Jun. 3, 2022.
German Office Action for German Application No., 10 2022 205 662.0 mailed Feb. 3, 2023, with English translation.

* cited by examiner

SYSTEM FOR POSITIONING A MEDICAL OBJECT AT A DESIRED DEPTH AND METHOD FOR EMITTING A LIGHT DISTRIBUTION

This application claims the benefit of German Patent Application No. DE 10 2022 205 662.0, filed on Jun. 2, 2022, which is hereby incorporated by reference in its entirety.

BACKGROUND

The present embodiments relate to a system for positioning a medical object at a desired depth, to a method for emitting a light distribution, and to a computer program product.

For treatment and/or examination of an examination object, a medical object (e.g., a needle and/or an endoscope) may be introduced up to a desired depth (e.g., a target positioning), partially into the examination object. To minimize injury to the examination object, precise adherence to the desired depth (e.g., not overshooting the desired depth) is very important. The desired depth is frequently specified with respect to an entry point of the medical object into the examination object. In order to display an insertion depth (e.g., instantaneous insertion depth) of the medical object into the examination object (e.g., a scale, such as a centimeter or millimeter scale) may be applied to a surface of the medical object. It is possible for a medical operator to read off the insertion depth at a point on the scale that is arranged at the entry point of the medical object into the examination object. Owing to the absence of a reference mark for the desired depth on the scale, this display is often susceptible to faulty operation by the medical operator. Alternatively, a marking may be applied to the medical object (e.g., by the medical operator). The marking is to be arranged at the entry point for attaining the desired depth. The marking that is to be arranged at the entry point may, however, be concealed by further medical objects (e.g., a guide facility and/or an introducer sheath). In addition, the desired depth with respect to the entry point may change during introduction of the medical object into the examination object (e.g., due to tissue deformation of the examination object, such as due to an interaction with the medical object and/or a physiological movement of the examination object). The fixed marking on the medical object cannot be flexibly adjusted to a change in the desired depth. This may result in incorrect positioning of the medical object in the examination object.

SUMMARY AND DESCRIPTION

The scope of the present invention is defined solely by the appended claims and is not affected to any degree by the statements within this summary.

The present embodiments may obviate one or more of the drawbacks or limitations in the related art. For example, precise and flexible positioning of a medical object at a desired depth in an examination object is provided.

The present embodiments relate, in a first aspect, to a system for positioning a medical object at a desired depth. The system includes a light guiding facility and a processing unit (e.g., including one or more processors). The processing unit is configured to receive planning information that specifies a desired depth for an arrangement of a predefined section of the medical object in an examination object with respect to an entry point of the medical object into the examination object. The medical object has a mark that has a predefined relative positioning with respect to the predefined section. The processing unit is also configured to control the light guiding facility for emitting a light distribution as a function of the planning information and the predefined relative positioning such that the light distribution illuminates the mark if the predefined section is arranged at the desired depth.

The medical object may include a surgical instrument (e.g., a needle, such as a puncture needle), and/or a trephine, and/or a diagnostic instrument (e.g., an endoscope, such as a laparoscope), and/or a catheter. In one embodiment, the medical object may be configured to be at least partially (e.g., completely) rigid and/or flexible. Further, the medical object may be configured to be at least partially (e.g., completely) elongated. Further, the medical object may have the predefined section. The predefined section may be, for example, a distal section of the medical object (e.g., a tip and/or an end section of the medical object). The medical object may be configured to be introduced at least partially into the examination object via the entry point at a surface of the examination object (e.g., the surface of the skin). For example, the predefined section of the medical object may be configured to be arranged in the examination object. In an operating state of the system, the medical object may be introduced into the examination object at the entry point such that the predefined section is arranged in the examination object.

The mark may be arranged on the medical object in a predefined relative positioning (e.g., a spatial relative position and/or relative orientation and/or relative pose) with respect to the predefined section, and/or be the mark may be at least partially (e.g., completely) integrated in the medical object. The mark may be arranged in a stationary or movable manner on the medical object (e.g., along a longitudinal extension direction of the medical object) with respect to the predefined section, and/or the mark may be at least partially integrated in the medical object. In addition, the mark may be fixed to the medical object (e.g., at a handle region and/or a proximal section of the medical object). With a substantially elongated embodiment of the medical object, the mark may be arranged at a distance along a longitudinal extension direction of the medical object with respect to the predefined section. For example, the mark may be arranged on a shaft of the medical object. In one embodiment, the mark may be arranged with respect to the predefined section such that the mark is arranged extracorporeally (e.g., outside of the examination object and/or at a distance from the entry point) if the predefined section is arranged at the desired depth. This may provide that the mark may be illuminated by the light distribution if the medical object is arranged at least partially in the examination object (e.g., if the predefined section is arranged at the desired depth). In one embodiment, the medical object may also have a scale (e.g., on a surface of the medical object) that displays a distance with respect to the mark along a longitudinal extension direction of the medical object (e.g., a centimeter or millimeter scale). The scale may be arranged along the longitudinal extension direction of the medical object below and/or above the mark. With an arrangement of the predefined section in the examination object that deviates from the desired depth, the light distribution may illuminate a scale element of the scale and hereby display (e.g., quantitatively) the deviation with respect to the desired depth as a distance between the mark and the illuminated scale element.

The examination object may be, for example, a human and/or animal female patient and/or a human and/or animal male patient and/or an examination phantom.

The processing unit may be configured to receive the planning information that has a specification relating to the desired depth. Receiving the planning information may, for example, include capturing and/or reading out a computer-readable data memory and/or receiving from a data storage unit (e.g., a database). Further, the planning information may be supplied by a supply unit of a medical imaging device. The planning information may include a, for example, preprocedural representation of the examination object (e.g., a mapping, such as medical image data) and/or a model of the examination object. The representation of the examination object may be two-dimensionally (2D) and/or three-dimensionally spatially resolved (3D). Further, the planning information may have the specification of the desired depth (e.g., with respect to the preprocedural representation of the examination object). The desired depth may be specified as a pair of points, including a target positioning of the predefined section and an entry point (e.g., a planned entry point) of the medical object into the examination object (e.g., with respect to the representation of the examination object).

The desired depth may describe a spatial distance between the predefined section (e.g., a reference point at the predefined section) and the entry point of the medical object into the examination object. The desired depth may be specified along a longitudinal extension direction of the medical object (e.g., with a curved or straight-line embodiment of the medical object). For example, the processing unit may be configured to repeatedly receive the planning information. For example, the planning information may be repeatedly supplied in the case of a captured (e.g., physiological) movement of the examination object. The specified desired depth may in each case be adjusted to a most recently captured movement state of the examination object. The physiological movement may include, for example, an organ movement (e.g., a heart movement) and/or a breathing movement of the examination object.

The light guiding facility may include a light source (e.g., a laser light source) that is configured to emit light distribution (e.g., predetermined light distribution). For this, the light guiding facility may include, for example, an optical diaphragm. The light distribution may include a predetermined distribution of laser light. The light distribution may project a predetermined light pattern (e.g., a line and/or a cross and/or a point). For example, the light source may include two laser light sources for emitting intersecting light fans. The light distribution may specify a desired positioning (e.g., a spatial position and/or orientation and/or pose) for the mark, at which the predefined section is arranged in the specified desired depth with respect to the entry point. The predetermined light pattern may be generated (e.g., supplied) by reflection and/or absorption of at least some of the predetermined light distribution by the mark. For example, the mark, at least in the case of illumination by the light distribution, may have an optically observable property.

In one embodiment, the processing unit may control the light guiding facility such that the light distribution illuminates the mark precisely if the predefined section of the medical object is arranged at the desired depth. For example, the light distribution does not illuminate the mark if the predefined section of the medical object is not arranged at the desired depth.

The processing unit may be configured to control the light guiding facility for emitting the light distribution as a function of the planning information and the predefined relative positioning. The light guiding facility may be configured to adjust emission of the light distribution (e.g., a direction and/or an angle of opening of the light distribution) as a function of the control of the processing unit.

This may enable precise and flexible positioning of the predefined section of the medical object at the desired depth in the examination object. For example, in the case of a planned movement of the medical object (e.g., a gradual retraction movement of the predefined section), emission of the light distribution may be adjusted at the respective desired depth of the planned movement (e.g., along a longitudinal extension direction of the medical object). Adjusted emission of the light distribution may assist the medical operator in a gradual arrangement of the predefined section at the desired depths of the planned movement. This may enable, for example, an advanced shaping of an ablation zone during an ablation procedure on the examination object.

In a further embodiment of the system, the system may also include a capturing unit that is configured to capture a positioning of the predefined section. Further, the processing unit may be configured to control the light guiding facility for emitting the light distribution additionally as a function of the positioning.

The capturing unit may be configured to capture the positioning (e.g., a spatial position and/or orientation and/or pose) of the predefined section of the medical object. The capturing unit may have, for example, an optical, and/or acoustic (e.g., ultrasound-based), and/or electromagnetic, and/or mechanical sensor that is configured to capture the positioning (e.g., instantaneous positioning) of the predefined section. For example, the capturing unit may have a camera (e.g., a 2D and/or 3D camera), and/or a medical imaging device, and/or an electromagnetic positioning system. Further, the capturing unit may be configured to supply the captured positioning of the predefined section of the medical object to the processing unit.

In one embodiment, the processing unit may be configured to register the planning information with the captured positioning of the predefined section (e.g., in a shared coordinate system, such as a coordinate system of the examination object or a coordinate system of the capturing unit). The planning information may be registered with the captured position of the predefined section (e.g., using the entry point of the medical object into the examination object). Further, the processing unit may be configured to control the light guiding facility for emitting the light distribution additionally as a function of the captured positioning of the predefined section.

The emission of the light distribution may also be adjusted to the positioning (e.g., instantaneous positioning) of the predefined section hereby (e.g., in the case of a change in position of the medical object and/or of the examination object with respect to the light guiding facility).

In a further embodiment of the system, the capturing unit may include a medical imaging device. The medical imaging device may be configured to acquire medical image data having a mapping of the medical object and of the examination object and supply the medical image data to the processing unit. The processing unit may also be configured to capture the positioning of the predefined section of the medical object using the image data.

The medical imaging device may include, for example, a medical X-ray device (e.g., a medical C-arm X-ray device), and/or a computed tomography system (CT system), and/or a magnetic resonance tomography system (MRT system), and/or an ultrasound device, and/or a positron emission tomography system (PET system). The medical imaging device may be configured to acquire the medical image data having a mapping of the medical object (e.g., of the predefined section) and of the examination object. The medical image data may have a two-dimensionally (2D) or three-dimensionally (3D) spatially resolved mapping of the medical object and of the examination object. Further, the medical image data may map the medical object and the examination object in a time-resolved manner. For example, the medical image data may map the medical object and the examination object in the operating state of the system in which the medical object is arranged at least partially in the examination object. Further, the medical imaging device may be configured to supply (e.g., to transfer) the medical image data to the processing unit. For example, the medical imaging device may be configured to acquire the medical image data repeatedly and supply the medical image data repeatedly to the processing unit.

The processing unit may be configured to capture (e.g., to determine) the, for example, instantaneous positioning of the predefined section of the medical object (e.g., with respect to the examination object) using the medical image data. For example, the processing unit may be configured to capture the positioning of the predefined section with respect to the entry point of the medical object into the examination object using the medical image data. The processing unit may be configured to identify the mapping of the medical object (e.g., of the predefined section) in the medical image data. Identifying the mapping of the medical object (e.g., of the predefined section) in the medical image data may include identifying (e.g., segmenting) image points (e.g., pixels and/or voxels) of the medical image data. The image points map the medical object (e.g., the predefined section). The processing unit may, for example, be configured to identify the image points that map the medical object (e.g., the predefined section) using a comparison of image values of the image points with a specified threshold value. Further, the medical object (e.g., the predefined section) may have a marker structure that is mapped in the medical image data. The processing unit may be configured to identify the mapping of the marker structure in the medical image data. The processing unit may also be configured to identify a mapping of the entry point of the medical object into the examination object in the medical image data. For this, the processing unit may identify, for example, a mapping of a surface of the examination object (e.g., the surface of the skin) in the medical image data. The processing unit may capture (e.g., determine) the positioning of the predefined section of the medical object with respect to the entry point.

The embodiment may enable improved control of the emission of the light distribution additionally as a function of the positioning of the predefined section.

In a further embodiment of the system, the light guiding facility may be arranged on the capturing unit and/or be at least partially integrated in the capturing unit.

The light guiding facility may be arranged on the capturing unit (e.g., the medical imaging device, using a holding apparatus, such as a joint, and/or a stand, and/or a robotic arm, and/or a holding arm, and/or a fixing device). For example, the light guiding facility may be mounted (e.g., robotically, movably, such as pivotally and/or rotatably and/or translationally) on the capturing unit by the holding apparatus and/or the fixing device. The processing unit may be configured for control of a movement (e.g., robotic movement) of the light guiding facility in order to adjust the light distribution.

Alternatively or in addition, the light guiding facility may be integrated at least partially (e.g., completely) in the capturing unit (e.g., the medical imaging device). For example, the light guiding facility may be integrated in a housing of the capturing unit (e.g., of the medical imaging device).

If the capturing unit includes a medical X-ray device and/or a CT system, the light guiding facility may be arranged, for example, on a source or a detector of the medical X-ray device and/or be integrated in the source or the detector. The capturing unit (e.g., the medical imaging device) may have an isocenter (e.g., a center of rotation). In one embodiment, the light guiding facility may be arranged on the capturing unit (e.g., the medical imaging device) and/or be at least partially integrated in the capturing unit such that the light distribution illuminates (e.g., with a light pattern) an object that is arranged in the isocenter. The capturing unit (e.g., the medical imaging device) may be repositionable with respect to the examination object such that the light distribution illuminates the mark if the predefined section is arranged at the desired depth and the mark is arranged in the isocenter of the capturing unit.

The embodiment may enable an inherent registering between a coordinate system of the light guiding facility and a coordinate system of the capturing unit. Further, the captured positioning of the predefined section may be inherently registered with the coordinate system of the light guiding facility hereby.

In a further embodiment of the system, the capturing unit may also be configured to capture a positioning of the examination object. The processing unit may also be configured to register the planning information with the positioning of the examination object.

The sensor for capturing the positioning of the predefined section of the medical object may also be configured for capturing the positioning of the examination object. Alternatively, the capturing unit may have a further (e.g., optical, and/or acoustic, such as ultrasound-based, and/or electromagnetic, and/or mechanical) sensor that is configured to capture an instantaneous positioning (e.g., a spatial position, and/or orientation, and/or pose) of the examination object. For example, the capturing unit may have a further camera (e.g., a 2D and/or 3D camera), and/or the medical imaging device, and/or a further electromagnetic positioning system. Further, the capturing unit may be configured to supply the captured positioning of the examination object to the processing unit.

The processing unit may also be configured to register the planning information (e.g., the specification relating to the desired depth) with the positioning of the examination object. For example, the capturing unit may be configured to capture a positioning of the entry point of the medical object into the examination object and/or of a tissue in which the target positioning is arranged. Further, the capturing unit may be configured to register the planning information (e.g., the specification relating to the desired depth) using the positioning of the entry point and/or of the tissue with the positioning (e.g., instantaneous positioning) of the examination object.

Emission of the light distribution may be adjusted hereby as a function of the registered planning information to the positioning (e.g., instantaneous positioning) of the examination object (e.g., of the entry point).

In a further embodiment of the system, the capturing unit may also be configured to identify the medical object and supply Information relating to the identification of the medical object to the processing unit. The processing unit may also be configured to determine the predefined relative positioning of the mark with respect to the predefined section using the identification of the medical object.

In one embodiment, the capturing unit may be configured to identify the medical object (e.g., a type, and/or a material property, and/or an operating parameter, and/or a geometric property, such as a size, and/or length, and/or shape, and/or thickness, and/or a diameter, of the medical object). The sensor for capturing the positioning of the predefined section of the medical object may be configured to identify the medical object. Alternatively or in addition, the capturing unit may have a further sensor that is configured to identify the medical object. For example, the processing unit may be configured to identify the medical object using geometric features (e.g., a contour, and/or shape), and/or a material property (e.g., a susceptibility), and/or a marker structure (e.g., a barcode and/or QR code), and/or electromagnetic identifiers, (e.g., a radio frequency identification system (RFID system)).

The capturing unit may also be configured to supply (e.g., transfer) the information relating to the identification of the medical object to the processing unit. The processing unit may also be configured to determine the predefined relative positioning of the mark with respect to the predefined section using the identification of the medical object (e.g., using the Information relating to the identification of the medical object). The processing unit may receive a catalog including information relating to the predefined relative positioning of the mark with respect to the predefined section for different medical objects. Using the catalog, the processing unit may determine the predefined relative positioning of the mark with respect to the predefined section for the identified medical object.

Alternatively or in addition, the capturing unit may include an input unit (e.g., a keyboard), and/or an input display, and/or a speech recognition system that is configured to capture a user input. The capturing unit may be configured to identify the medical object using the user input. The user input may also include information relating to the relative positioning of the mark with respect to the predefined section. Alternatively, the processing unit may be configured to determine the relative positioning using the identification of the medical object and a catalog. The catalog includes information relating to the predefined relative positioning of the mark with respect to the predefined section for different medical objects.

The embodiment may enable reliable determination of the relative positioning of the mark with respect to the predefined section.

In a further embodiment of the system, the planning information may also specify a desired path for the arrangement of the medical object. The light guiding facility may be configured to emit a further light distribution that illuminates the medical object with a predefined light pattern if the medical object is arranged on the desired path.

The desired path may specify a trajectory (e.g., a three-dimensional and/or straight-line trajectory) for the medical object (e.g., with respect to the examination object, such as in the coordinate system of the examination object). In one embodiment, the light guiding facility may be configured to emit the further light distribution using the light source and/or a further light source. The further light distribution may include a conventional light distribution of a conventional light source for representing a desired path (e.g., a needle path). For example, the further light distribution may include a further distribution of laser light. The further light distribution may project a further light pattern (e.g., intersecting lines and/or a point). For example, the further light source may include two laser light sources for emitting light fans that intersect along the desired path. The desired path, along which the medical object is to be arranged, may be projected via the further light distribution. The further light pattern may be generated (e.g., supplied) by reflection and/or absorption of at least some of the further light distribution by the medical object.

This may enable precise and flexible positioning of the predefined section at the desired depth and of the medical object along the desired path.

In a further embodiment of the system, the light guiding facility may be mounted in a movable manner with respect to the examination object. The light guiding facility may be arranged in a first positioning for emitting the light distribution. Further, the light guiding facility may be arranged in a further positioning (e.g., a second positioning) for emitting the further light distribution. The second positioning is different than the first positioning.

In one embodiment, the light guiding facility may be mounted in a movable manner (e.g., in a translational and/or rotational manner) with respect to the examination object. If the capturing unit includes a movable medical imaging device (e.g., a medical C-arm X-ray device) and the light guiding facility is arranged on the medical imaging device and/or is at least partially integrated in the medical imaging device, the light guiding facility may also be moved in the case of a movement of the medical imaging device with respect to the examination object. For example, the light guiding facility may be arranged on a source or a detector of the medical C-arm X-ray device and be moved (e.g., rotated) with respect to the examination object by a rotational movement of a C-arm that holds the source and the detector. The light guiding facility may be arranged in a predefined relative position with respect to the medical imaging device (e.g., with respect to the source and of the detector).

Alternatively or in addition, the light guiding facility may have a motion unit that mounts the light guiding facility in a movable manner. The motion unit may be configured to enable a movement (e.g., a manual and/or robotic movement; a translation and/or rotation) of the light guiding facility.

In one embodiment, for emitting the light distribution, the light guiding facility may be arranged in a first positioning (e.g., a first spatial position and/or orientation and/or pose, such as with respect to the examination object). For example, the light guiding facility may be arranged in the first positioning in a first operating state of the system and emit the light distribution.

Further, for emitting the further light distribution, the light guiding facility may be arranged in a further positioning (e.g., a further spatial position and/or orientation and/or pose, such as with respect to the examination object). The further positioning may be at least partially (e.g., completely) different than the first positioning. For example, in a further operating state of the system, the light guiding facility may be arranged in the further positioning and emit the further light distribution. The light guiding facility may be configured to be moved (e.g., manually and/or robotically) from the first positioning into the further positioning, or vice versa. For example, the light guiding facility may be configured to be moved (e.g., repositioned repeatedly between the first positioning and the further positioning). This may enable alternate (e.g., alternating) emission of the light distribution and the further light distribution by the light guiding facility in the respective positioning (e.g., the first positioning and the further positioning). For example, the light guiding facility may be rotatably mounted about an isocenter (e.g., a center of rotation). The first positioning and the further positioning may be arranged around the isocenter on a radius of a circular path (e.g., trajectory) of the light guiding facility in each case. In addition, both the light distribution and the further light distribution may illuminate the isocenter.

In one embodiment, the first positioning may be arranged with respect to the examination object such that with an arrangement of the medical object on the desired path, the mark may be illuminated by the light distribution. The first positioning may be arranged (e.g., at a distance, such as laterally) from the desired path (e.g., progression view). Further, the light guiding facility may be configured to emit the light distribution so that the light distribution is not parallel to the desired path.

The further positioning may be arranged at a distance from the entry point of the medical object into the examination object (e.g., the further positioning may be arranged along the desired path (bulls-eye view)). Further, the light guiding facility may be configured to emit the further light distribution at least partially (e.g., completely) parallel to the desired path.

This may enable both the specification of the desired depth and of the desired path by, for example, sequential and/or alternating emission of the light distribution and the further light distribution by the light guiding facility (e.g., extremely cost-efficiently).

In a further embodiment of the system, the mark may be configured as a structural element, and/or graphical element, and/or light-reflecting element, and/or light-absorbing element on a surface of the medical object.

The mark may be configured as a structural element (e.g., a recess, and/or elevation, and/or edge such as on a surface of the medical object). Alternatively or in addition, the mark may be configured as a graphical element (e.g., as a pattern, and/or line, and/or strip, and/or cross) on the surface of the medical object. Alternatively or in addition, the mark may be configured as a light-reflecting element (e.g., as a reflector) and/or as a light-absorbing element (e.g., black, such as jet black, coating) on the surface of the medical object. The light-reflecting element may be configured for at least partial (e.g., complete) reflection of the light distribution. Further, the light-absorbing element may be configured for at least partial (e.g., complete) absorption of the light distribution. In one embodiment, the light-reflecting element may have a reflectivity at least partially different than the surface of the medical object (e.g., with respect to the light distribution). Further, the light-absorbing element may have an absorptivity at least partially different than the surface of the medical object (e.g., respect to the light distribution).

The illumination of the mark by the light distribution may hereby be captured by an optical sensor and/or the medical operator.

In a further embodiment of the system, the medical object may have a plurality of marks that each have a predefined relative positioning with respect to the predefined section. The plurality of marks may have, at least in the case of illumination by the light distribution, an optically distinguishable property. The processing unit may be configured to identify one mark of the plurality of marks as the mark to be illuminated using the planning information. Further, the processing unit may be configured to control the light guiding facility for emitting the light distribution such that the light distribution illuminates the identified mark if the predefined section is arranged at the desired depth.

In one embodiment, the medical object may have a plurality of marks that may be configured to be at least partially (e.g., completely) identical or different. The plurality of marks may have different relative positionings with respect to the predefined section (e.g., along a longitudinal extension direction of the medical object). The plurality of marks may be uniformly or irregularly arranged at a distance from one another along the longitudinal extension direction of the medical object.

The plurality of marks may each have one optical property (e.g., a reflectivity, and/or absorptivity, and/or color, and/or geometric property, such as a shape, and/or numbering, and/or writing) that is distinguishable, at least with illumination by the light distribution (e.g., with respect to the other marks of the plurality of marks). In one embodiment, the optical property of the plurality of marks may also be distinguishable in the absence of illumination by the light distribution. In one embodiment, the optical property of the plurality of marks may be distinguished via an optical sensor and/or the medical operator.

The processing unit may be configured to identify one mark of the plurality of marks as the mark to be illuminated by the light distribution using the planning information. The planning information may have the specification for the desired depth of the arrangement of the predefined section in the examination object with respect to the entry point of the medical object. The processing unit may identify the mark to be illuminated (e.g., via a comparison of the different relative positionings of the plurality of marks with respect to the predefined section with the desired depth specified by the planning information). For example, a minimum distance may be specified between the mark to be illuminated and the entry point of the medical object into the examination object. The processing unit may then the identify the mark of the plurality of marks as the mark to be illuminated, which, owing to its relative positioning with respect to the predefined section with the arrangement of the predefined section at the desired depth, has at least the minimum distance with respect to the entry point and/or comes spatially closest to this minimum distance, (e.g., extracorporeally). The processing unit may be configured to receive information relating to the plurality of marks (e.g., the relative positionings of the plurality of marks with respect to the predefined section). For example, the processing unit may be configured to receive and/or determine the information relating to the plurality of marks using the identification of the medical object.

Further, the processing unit may be configured to control the light guiding facility such that the light distribution illuminates the identified mark (e.g., only the identified mark) with the arrangement of the predefined section at the desired depth (e.g., only with the arrangement of the predefined section at the desired depth).

With the embodiment, the medical object, having the plurality of markings, may be used for the arrangement of the predefined section at different desired depths.

The present embodiments relate, in a second aspect, to a method for emitting a light distribution. In a first act, planning information is received. The planning information specifies a desired depth for an arrangement of a predefined section of a medical object in an examination object with respect to an entry point of the medical object into the examination object. The medical object has a mark that has a predefined relative positioning with respect to the predefined section. In a further act, a light distribution is emitted by a light guiding facility as a function of the planning information and the predefined relative positioning such that the mark is illuminated if the predefined section is arranged at the desired depth.

The advantages of the method substantially correspond to the advantages of the system for positioning a medical object at a desired depth. Features, advantages, or alternative embodiments mentioned in this connection may likewise also be transferred to the other subject matters, and vice versa.

In a further embodiment of the method, a positioning of the predefined section may be captured. The light distribution may also be emitted as a function of the positioning.

In a further embodiment of the method, the medical object may be identified. The predefined relative positioning of the mark with respect to the predefined section may be determined using the identification of the medical object.

In a further embodiment of the method, the planning information may also specify a desired path for the arrangement of the medical object. A further light distribution may be emitted by the light guiding facility such that the medical object is illuminated by a predefined light pattern if the medical object is arranged on the desired path.

In a further embodiment of the method, the medical object may have a plurality of marks that each have a predefined relative positioning with respect to the predefined section. The plurality of marks may have, at least with illumination by the predefined light distribution, an optically distinguishable property. In addition, one mark of the plurality of marks may be identified as the mark to be illuminated using the planning information. In one embodiment, the light distribution may be emitted such that the light distribution illuminates the identified mark if the predefined section is arranged at the desired depth.

According to a further embodiment of the method, the method may include arranging the predefined section of the medical object in an initial positioning in the examination object, with the medical object being introduced into the medical object at the entry point. Further, the predefined section may be repositioned from the initial positioning in a target positioning such that the light distribution illuminates the mark, with the predefined section having the desired depth with respect to the entry point in the target positioning.

The present embodiments relate in a third aspect to a computer program product having a computer program that may be loaded directly into a memory of a processing unit, having program segments in order to carry out all acts of a proposed method for emitting a light distribution when the program segments are executed by the processing unit.

The present embodiments may also relate to a computer-readable storage medium (e.g., a non-transitory computer-readable storage medium) on which program segments that may be read and executed by a processing unit are stored in order to carry out all acts of the method for emitting a light distribution when the program segments are executed by the processing unit.

An implementation largely in terms of software has the advantage that even previously used processing units may be easily retrofitted by a software update in order to operate inventively. Apart from the computer program, a computer program product of this kind may optionally include additional component parts, such as documentation and/or additional components, as well as hardware components, such as hardware keys (e.g., dongles, etc.) in order to use the software.

BRIEF DESCRIPTION OF THE DRAWINGS

Embodiments of the invention are represented in the drawings and will be described in more detail below. Same reference numerals will be used in different figures for same features.

In the drawings.

DETAILED DESCRIPTION

Figure 1:
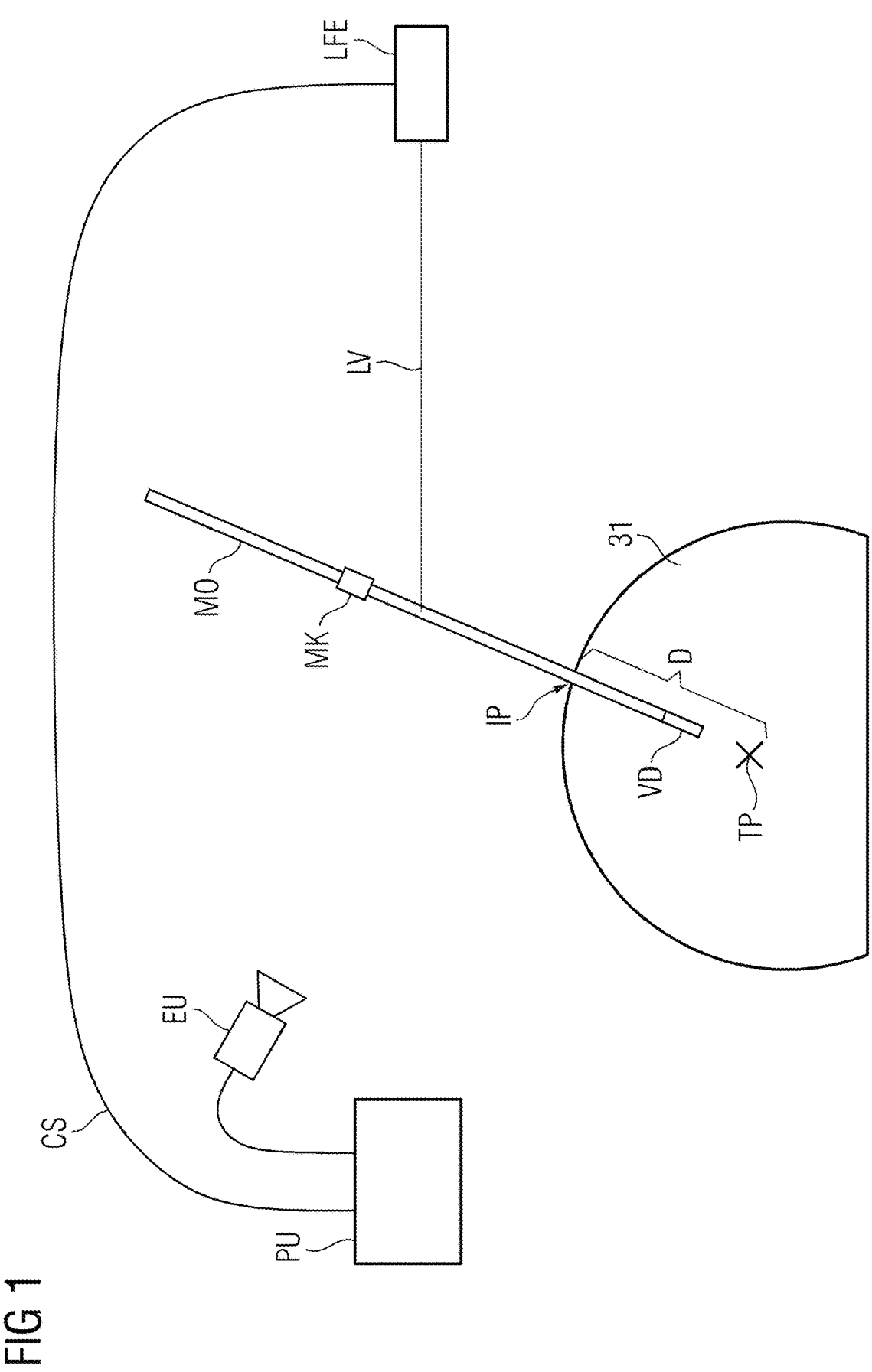
FIGS. 1 and 2 show schematic representations of different operating states of one embodiment of a system.
Figure 2:
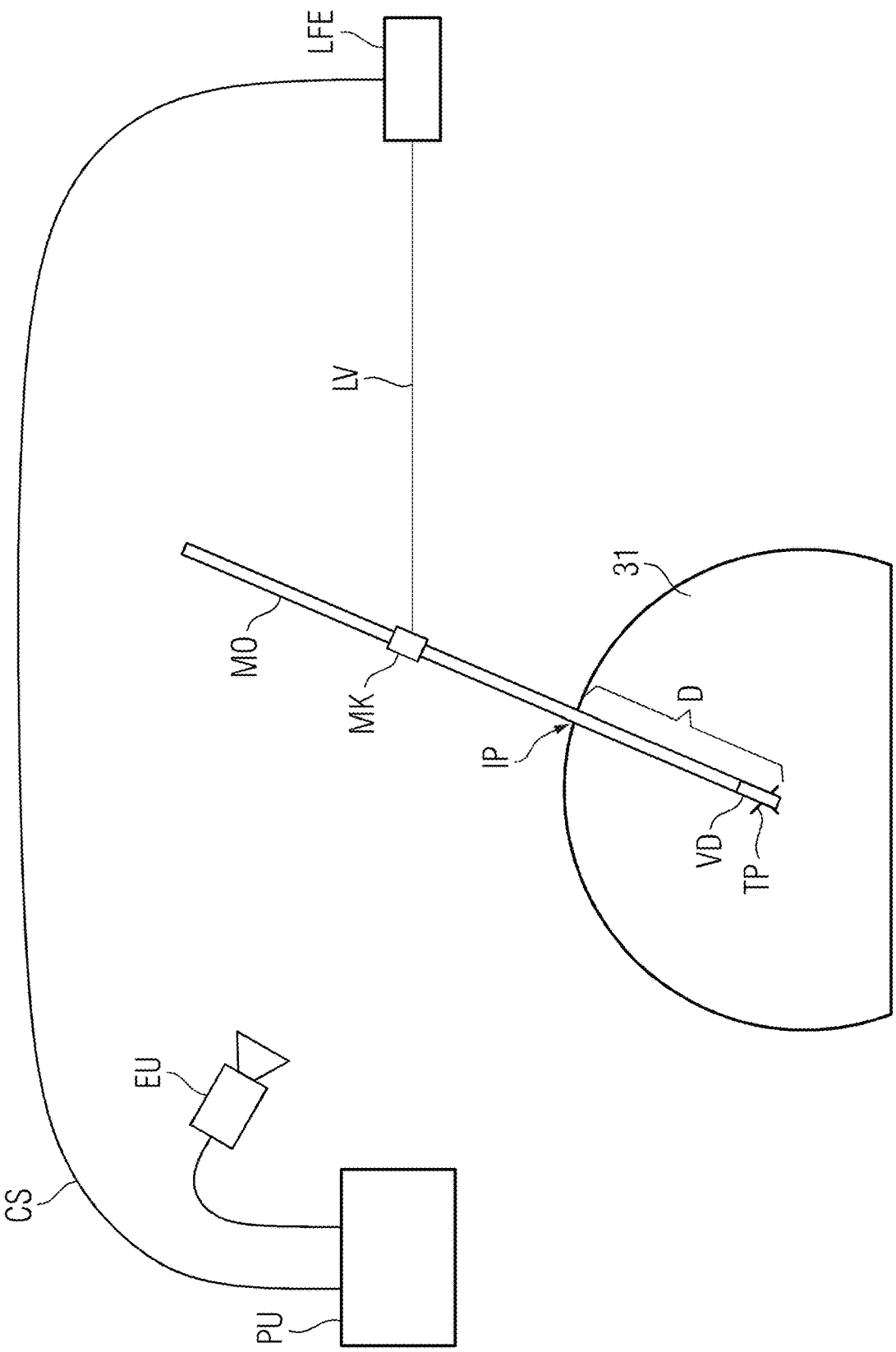

FIGS. 1 and 2 show schematic representations of different operating states of one embodiment of a system for positioning a medical object MO at a desired depth D. The system may include a light guiding facility LFE and a processing unit PU. The processing unit PU may be configured to receive REC-PLI planning information PLI that specifies a desired depth D for an arrangement of a predefined section VD of the medical object MO in an examination object 31 with respect to an entry point IP of the medical object MO into the examination object 31. Further, the medical object MO may have a mark MK that has a predefined relative positioning with respect to the predefined section VD. The mark MK may be configured as a structural element and/or graphical element and/or light-reflecting element and/or light-absorbing element on a surface of the medical object MO. The processing unit PU may also be configured to control the light guiding facility LFE for emitting a light distribution LV as a function of the planning information PLI and the predefined relative positioning such that the light distribution LV illuminates the mark MK when the predefined section VD is arranged at the desired depth D (e.g., by a signal CS).

In one embodiment, the system may also include a capturing unit EU that is configured to capture CAP-POS a positioning of the predefined section. The processing unit PU may be configured to control the light guiding facility LFE for emitting the light distribution LV additionally as a function of the captured positioning POS. In one embodiment, the capturing unit EU may also be configured to capture a positioning of the examination object 31. The processing unit PU may be configured to register the planning information PLI with the positioning of the examination object 31. Further, the processing unit PU may be configured to control the light guiding facility LFE for emitting the light distribution LV as a function of the registered planning information.

Further, the capturing unit EU may be configured to identify the medical object MO and supply information relating to the identification of the medical object MO to the processing unit PU. The processing unit PU may also be configured to determine the predefined relative positioning of mark MK with respect to the predefined section VD using the identification of the medical object MO.

In the operating state of the system represented in FIG. 1, the medical object MO may be partially introduced into the examination object 31 via the entry point IP. A depth of the predefined section VD (e.g., with respect to the entry point IP) may be less than the specified desired depth D, so that the light distribution LV does not illuminate the mark MK. For example, in this operating state, the predefined section is not arranged in the examination object 31 at a specified target positioning TP. FIG. 2 shows a further operating state of the system, with the predefined section VD being arranged at the desired depth D (e.g., at the target positioning TP). The light distribution LV illuminates the mark MK.

Figure 3:
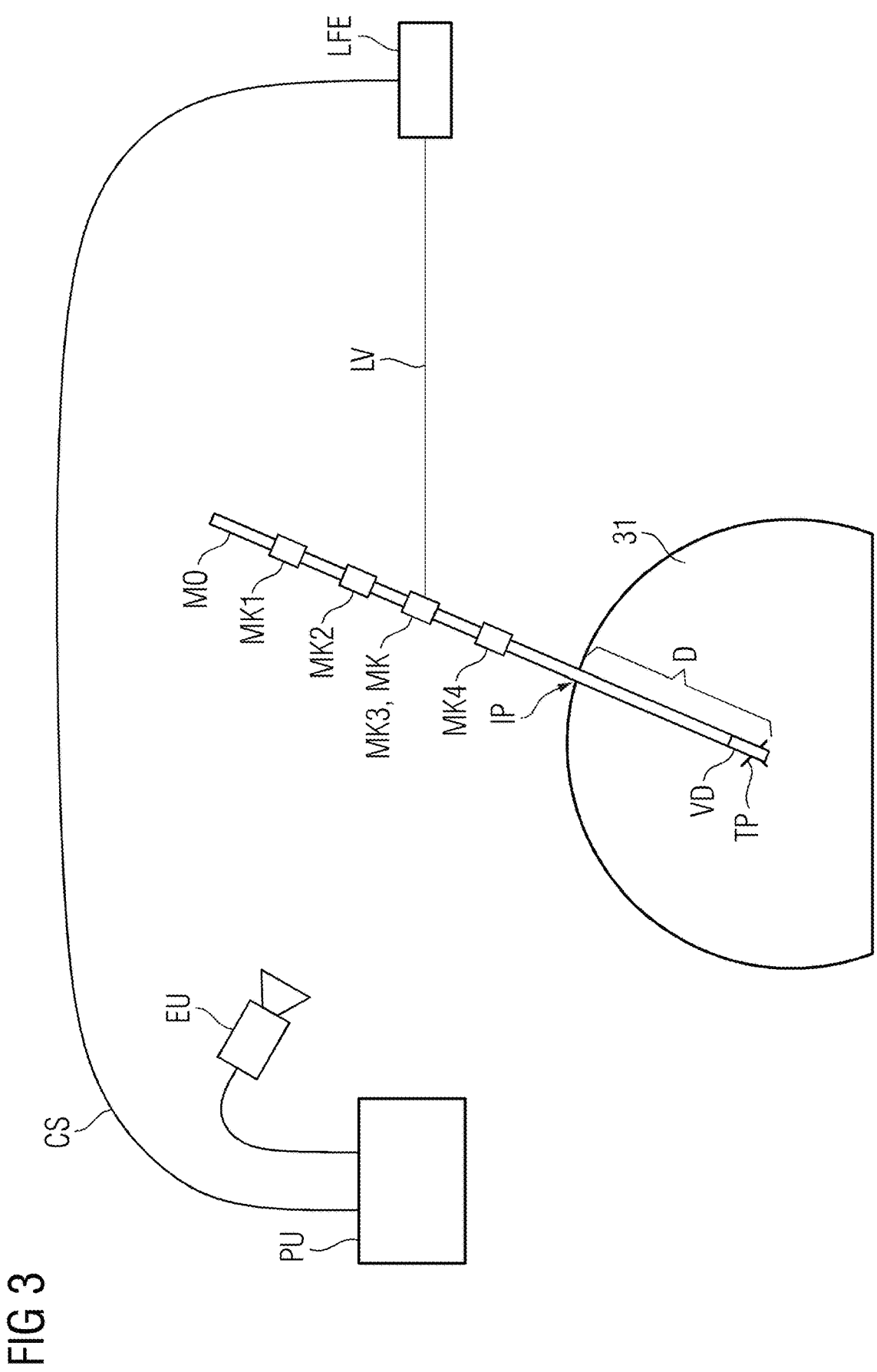
FIG. 3 shows a schematic representation of a further embodiment of a system.

FIG. 3 shows a schematic representation of a further embodiment of the system. The medical object MO may have a plurality of marks MK1, MK2, MK3 and MK4 that each have a predefined relative positioning with respect to the predefined section VD. Further, the plurality of marks MK1, MK2, MK3 and MK4, at least with illumination by the predefined light distribution LV, may have an optically distinguishable property. The processing unit PU may also be configured to identify one mark of the plurality of marks MK1, MK2, MK3 and MK4 (e.g., the mark MK3) as the mark to be illuminated MK using the planning information PLI. In addition, the processing unit PU may be configured to control the light guiding facility LFE for emitting the light distribution LV such that the light distribution LV illuminates the identified mark MK if the predefined section VD is arranged at the desired depth D.

Figure 4:
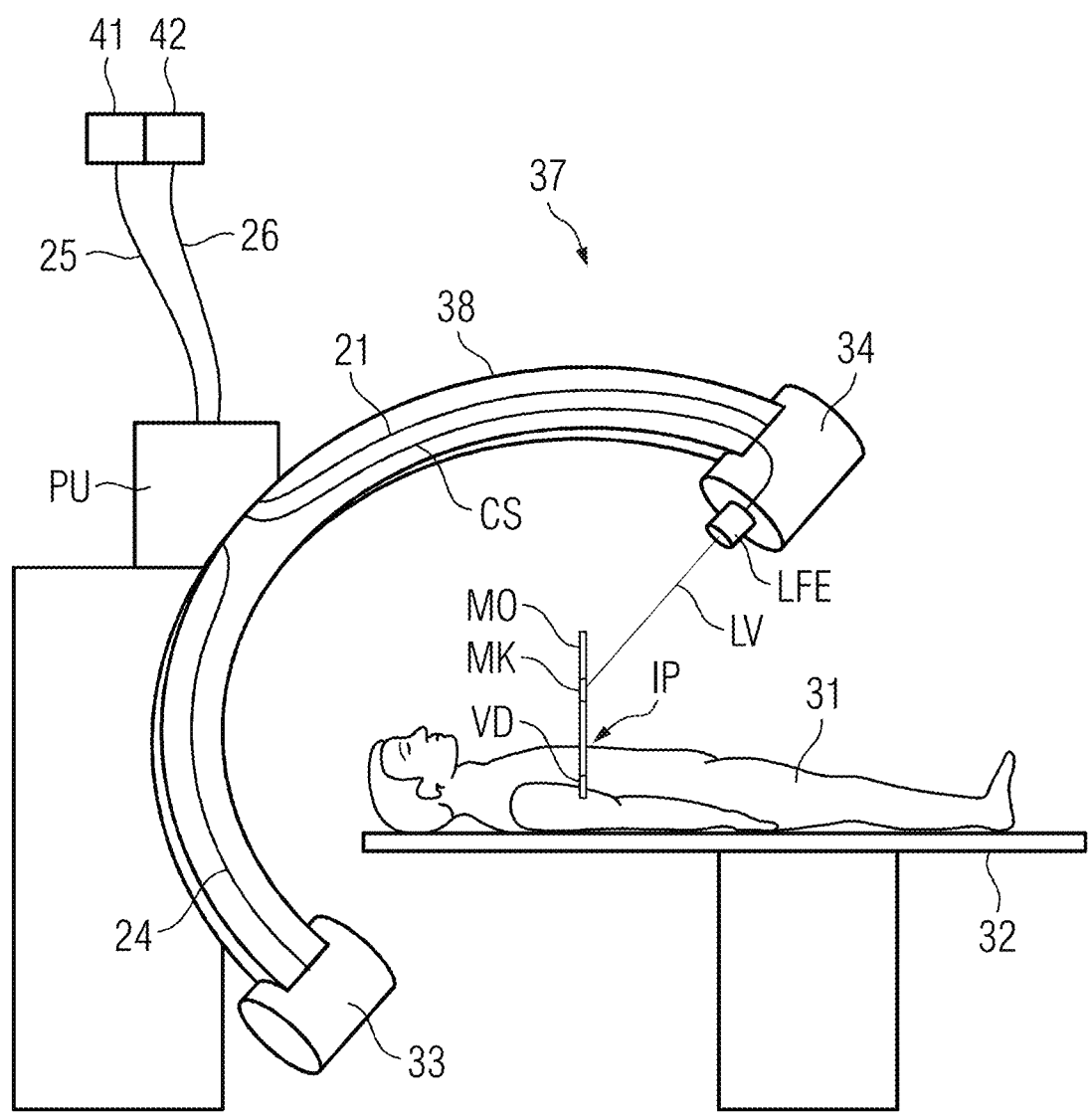
FIGS. 4 and 5 show schematic representations of different operating states of a further embodiment of a system.
Figure 5:
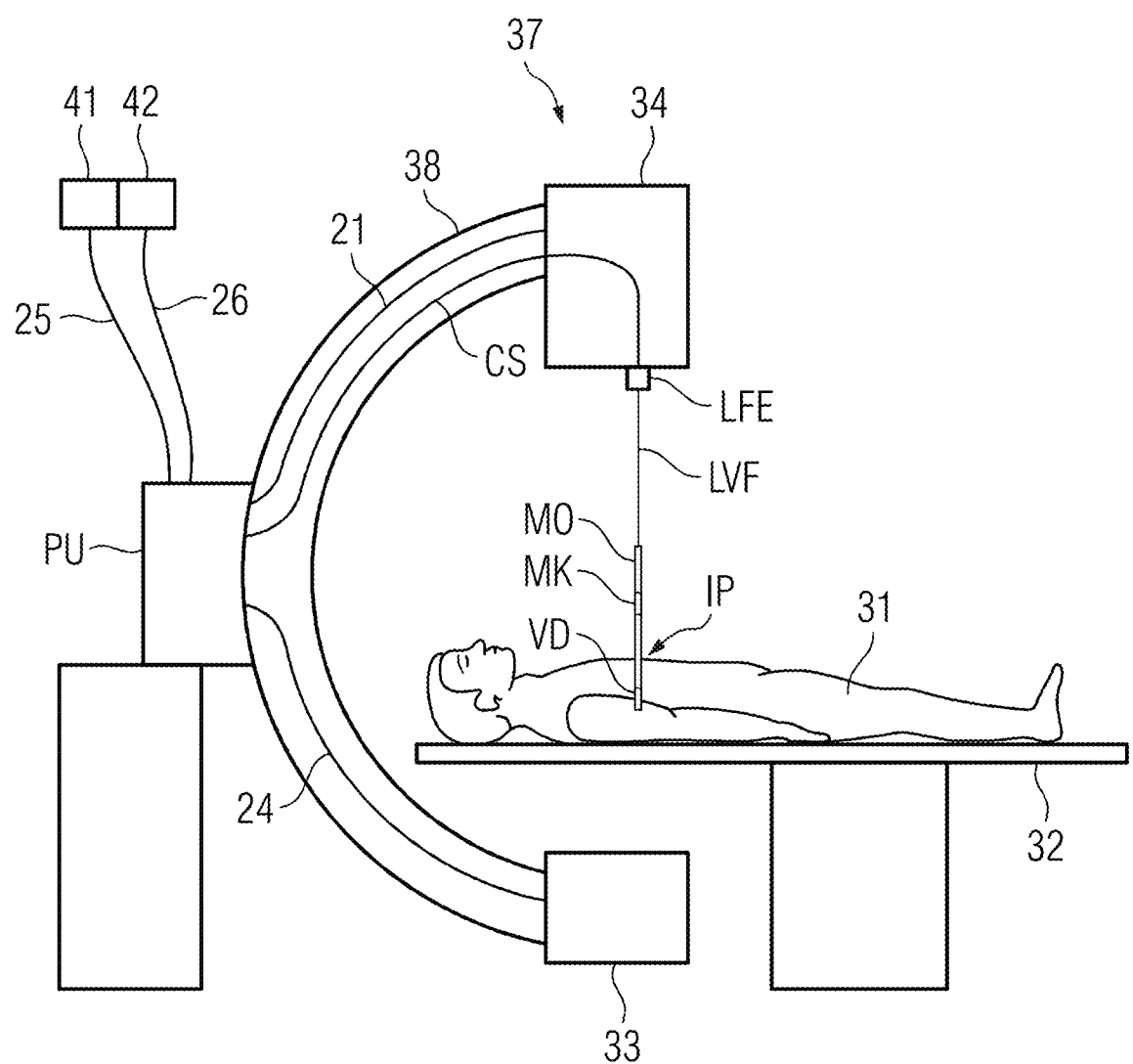

FIGS. 4 and 5 schematically represent different operating states of a further embodiment of the system. The capturing unit EU may include a medical imaging device (e.g., a medical C-arm X-ray device 37). The medical C-arm X-ray device 37 may be configured to acquire medical image data having a mapping of the medical object MO and of the examination object 31, and supply the medical image data to the processing unit PU. In an operating state of the system, the examination object 31 may be arranged on a patient support apparatus 32. The medical C-arm X-ray device 37 may have a detector 34 (e.g., an X-ray detector) and a source 33 (e.g., an X-ray source). For acquiring the medical image data of the examination object 31 and the medical object MO, the processing unit PU may send a signal 24 to the X-ray source 33. The X-ray source 33 may then emit an X-ray beam. On impingement of the X-ray beam, after interaction with the examination object 31 and the medical object MO, on a surface of the detector 34, the detector 34 may send a signal 21 to the processing unit PU. The processing unit PU may receive the medical image data with the aid of the signal 21. Further, the processing unit PU may be configured to capture the positioning POS of the predefined section VD of the medical object MO using the image data.

In one embodiment, the light guiding facility LFE may be arranged on the medical C-arm X-ray device 37 and/or be at least partially integrated in the medical C-arm X-ray device 37. The light guiding facility LFE may be mounted in a movable manner with respect to the examination object 31 (e.g., via a rotation of the C-arm 38). The C-arm 38 of the C-arm X-ray device 37 may be mounted in a movable manner around one or more axes. Further, the X-ray source 33 and the detector 34 may each be arranged at one end of the C-arm 38. In one embodiment, the light guiding facility LFE, as schematically represented in FIG. 4, may be arranged in a first positioning for emitting the light distribution LV. Further, the planning information PLI may specify a desired path for the arrangement of the medical object MO. The light guiding facility LFE may be configured to emit a further light distribution LVF, which illuminates the medical object MO with a predefined light pattern when the further light distribution LVF is arranged on the desired path. As schematically represented in FIG. 5, the light guiding facility LFE may be arranged in a further positioning (e.g., a second positioning) for emitting the further light distribution LVF. The second positioning differs from the first positioning.

The system may also have an input unit 42 (e.g., a keyboard) and a presentation unit 41 (e.g., a monitor and/or a display and/or a projector). The input unit 42 may be integrated in the presentation unit 41 (e.g., in the case of a capacitive and/or resistive input display). The input unit 42 may be configured for capturing a user input. For this, the input unit 42 may, for example, send a signal 26 to the processing unit PU. The processing unit PU may be configured to control the medical C-arm X-ray device 37 and/or the light guiding facility LFE as a function of the user input (e.g., as a function of the signal 26). The presentation unit 41 may be configured to display a graphical representation of the medical image data. For this, the processing unit PU may send a signal 25 to the presentation unit 41.

Figure 6:
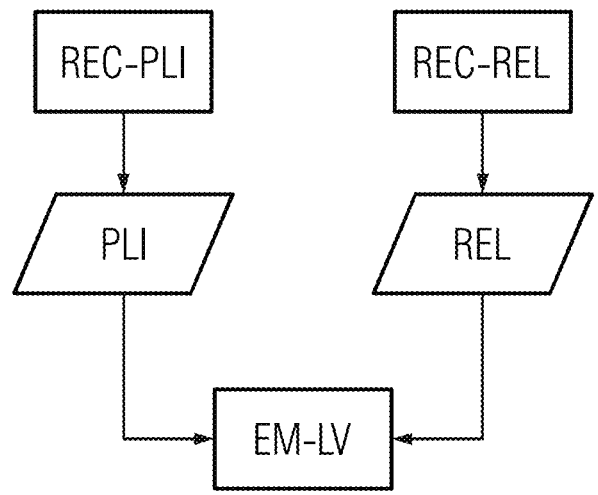
FIGS. 6 to 8 show schematic representations of different embodiments of a method for emitting a light distribution.

FIG. 6 schematically represents an embodiment of a method for emitting EM-LV a light distribution LV. The planning information PLI, which specifies the desired depth D for the arrangement of the predefined section VD in the examination object 31 with respect to the entry point IP of the medical object MO in the examination object 31, may be received REC-PLI. In addition, the light distribution LV may be emitted EM-LV by the light guiding facility LFE as a function of the planning information PLI and the predefined relative positioning such that the mark MK is illuminated if the predefined section VD is arranged at the desired depth D. In one embodiment, information relating to the relative positioning REL of the mark MK with respect to the predefined section VD may be received REC-REL (e.g., captured or determined).

Figure 7:
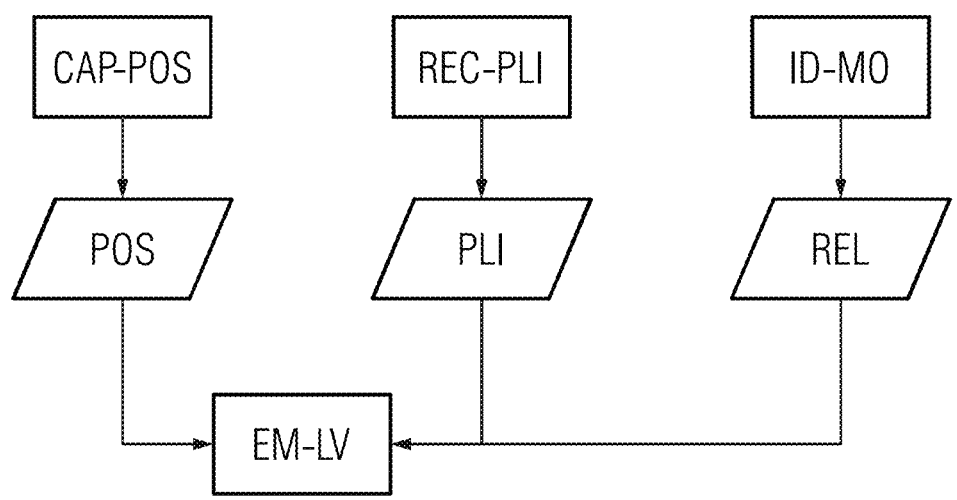

FIG. 7 schematically represents a further embodiment of the method for emitting EM-LV a light distribution LV. Medical image data BD having a mapping of the medical object MO and of the examination object 31 may be acquired ACQ-BD by a medical imaging device (e.g., by the medical C-arm X-ray device 37). Further, the positioning POS of the predefined section VD of the medical object MO may be captured CAP-POS using the image data BD. The medical object MO may be identified ID-MO in the process. Further, the predefined relative positioning of the mark MK with respect to the predefined section VD may be determined using the identification of the medical object MO.

Figure 8:
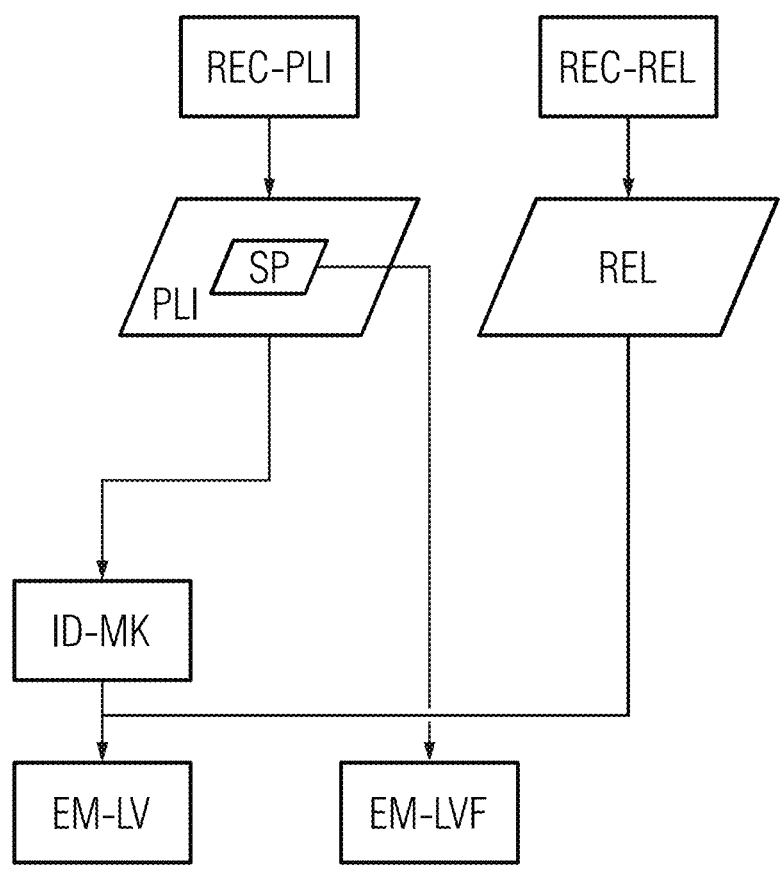

FIG. 8 shows a schematic representation of a further embodiment of the method for emitting EM-LV a light distribution LV. In one embodiment, the planning information PLI may also specify the desired path SP for the arrangement of the medical object MO. The further light distribution LVF may be emitted by the light guiding facility LFE such that the medical object MO is illuminated by the predefined light pattern when the medical object MO is arranged on the desired path SP.

Further, the medical object MO may have a plurality of marks MK1, MK2, MK3 and MK4 that each have a predefined relative positioning with respect to the predefined section VD. The plurality of marks MK1, MK2, MK3 and MK4, at least with illumination by the predefined light distribution, may have an optically distinguishable property. Further, one of the marks MK1, MK2, MK3 and MK4 (e.g., the mark MK3) may be identified ID-MK as the mark to be illuminated MK. The light distribution LV may be emitted EM-LV such that the light distribution illuminates the identified mark MK if the predefined section VD is arranged at the desired depth D.

The schematic representations contained in the described figures do not represent any kind of scale or size ratios.

The preceding methods and apparatuses described in detail are merely embodiments that a person skilled in the art may modify in a wide variety of ways without departing from the scope of the invention. Further, use of the indefinite article "a" or "an" does not preclude the relevant features from also being present multiple times. Similarly, the terms "units" and "element" do not preclude the relevant components from being composed of a plurality of cooperating sub-components that may optionally also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A system for positioning a medical object at a desired depth, the system comprising:
   a light guiding facility; and
   a processing unit configured to receive planning information that specifies a desired depth for an arrangement of a predefined section of a medical object in an examination object with respect to an entry point of the medical object into the examination object,
   wherein the medical object has a mark that has a predefined relative positioning with respect to the predefined section, and
   wherein the processing unit is further configured to control the light guiding facility for emitting a light distribution as a function of the planning information and the predefined relative positioning such that the light distribution illuminates the mark when the predefined section is arranged at the desired depth.

2. The system of claim 1, further comprising a capturing unit that is configured to capture a positioning of the predefined section,
   wherein the processing unit is further configured to control the light guiding facility for emitting the light distribution additionally as a function of the positioning.

3. The system of claim 2, wherein the capturing unit comprises a medical imaging device,
   wherein the medical imaging device is configured to acquire medical image data having a mapping of the medical object and of the examination object, and supply the acquired medical image data to the processing unit, and
   wherein the processing unit is further configured to capture the positioning of the predefined section of the medical object using the acquired medical image data.

4. The system of claim 2, wherein the light guiding facility is arranged on the capturing unit, is integrated at least partially in the capturing unit, or a combination thereof.

5. The system of claim 2, wherein the capturing unit is further configured to capture a positioning of the examination object, and
   wherein the processing unit is further configured to register the planning information with the positioning of the examination object.

6. The system of claim 1, further comprising a capturing unit that is configured to:
   identify the medical object; and
   supply information relating to the identification of the medical object to the processing unit,
   wherein the processing unit is further configured to determine the predefined relative positioning of the mark with respect to the predefined section using the identification of the medical object.

7. The system of claim 1, wherein the planning information also specifies a desired path for arrangement of the medical object, and
   wherein the light guiding facility is configured to emit a further light distribution that illuminates the medical object with a predefined light pattern when the medical object is arranged on the desired path.

8. The system of claim 7, wherein the light guiding facility is mounted to move with respect to the examination object,
   wherein the light guiding facility for emitting the light distribution is arrangeable in a first positioning, and
   wherein the light guiding facility for emitting the further light distribution is arrangeable in a second positioning, the second positioning being different than the first positioning.

9. The system of claim 1, wherein the mark is configured as a structural element, a graphical element, a light-reflecting element, a light-absorbing element, or any combination thereof on a surface of the medical object.

10. The system of claim 1, wherein the medical object has a plurality of marks, each mark of the plurality of marks having a predefined relative positioning with respect to the predefined section,
    wherein the plurality of marks, at least on illumination with the predefined light distribution, has an optically distinguishable property, and
    wherein the processing unit is further configured to:
    identify one mark of the plurality of marks using the planning information as the mark to be illuminated; and
    control the light guiding facility for emitting the light distribution such that the light distribution (illuminates the identified mark when the predefined section is arranged at the desired depth.

* * * * *